(12) United States Patent
Numajiri et al.

(10) Patent No.: US 6,454,722 B1
(45) Date of Patent: Sep. 24, 2002

(54) DOPPLER VELOCIMETER FOR BLOOD FLOW

(75) Inventors: Yasuyuki Numajiri, Kawasaki; Shinya Tanaka, Tokyo, both of (JP)

(73) Assignee: Canon Kabushiki Kaisha, Tokyo (JP)

( * ) Notice: Subject to any disclaimer, the term of this patent is extended or adjusted under 35 U.S.C. 154(b) by 5 days.

(21) Appl. No.: 09/650,348

(22) Filed: Aug. 29, 2000

(30) Foreign Application Priority Data

Aug. 31, 1999 (JP) ............................................. 11-245590
Apr. 4, 2000 (JP) ......................................... 2000-102240

(51) Int. Cl.7 ................................................. A61B 5/02
(52) U.S. Cl. ........................ 600/504; 600/558; 600/399
(58) Field of Search .............................. 600/504, 558, 600/399, 400, 404, 405; 351/221

(56) References Cited

U.S. PATENT DOCUMENTS

| | | | |
|---|---|---|---|
| 4,339,944 A | * 7/1982 | Abts | 73/19.03 |
| 4,830,483 A | 5/1989 | Kohayakawa et al. | 351/221 |
| 4,866,243 A | 9/1989 | Sakane et al. | 219/121.62 |
| 4,951,670 A | 8/1990 | Tanaka et al. | |
| 5,031,623 A | 7/1991 | Kohayakawa et al. | |
| 5,106,184 A | 4/1992 | Milbocker | 351/221 |
| 5,107,851 A | 4/1992 | Yano et al. | |
| 5,287,753 A | * 2/1994 | Routh et al. | 73/861.25 |
| 5,455,644 A | 10/1995 | Yazawa et al. | 351/206 |
| 5,615,683 A | 4/1997 | Toge et al. | |
| 5,894,337 A | 4/1999 | Okinishi et al. | 351/205 |
| 5,976,096 A | 11/1999 | Shimizu et al. | 600/504 |
| 6,022,321 A | * 2/2000 | Amano et al. | 600/500 |

FOREIGN PATENT DOCUMENTS

JP    2000-286946 A  * 10/2000  ............ A61B/5/02

* cited by examiner

Primary Examiner—Kevin Shaver
Assistant Examiner—Patricia Mallari
(74) Attorney, Agent, or Firm—Fitzpatrick, Cella, Harper & Scinto

(57) ABSTRACT

A Doppler velocimeter includes an illumination system for illuminating a blood vessel with a light beam, a detector for detecting Doppler-shifted scattered light produced from blood flowing in the blood vessel, and a processor for obtaining a blood flow velocity by analyzing a signal from said detector. The processor compares an actual power spectrum obtained by frequency-analyzing the signal with a theoretical power spectrum obtained using a frequency as a parameter while changing the parameter.

15 Claims, 11 Drawing Sheets

FLOW VELOCITY DISTRIBUTION

DOPPLER VELOCIMETER FOR BLOOD FLOW

BACKGROUND OF THE INVENTION

1. Field of the Invention

The present invention relates to a Doppler velocimeter useful for the measurement of the blood flow velocity in a blood vessel such as that on the fundus of an eyeball or the like and an eye examining apparatus, such as a fundus blood flow meter, or the like.

2. Related Background Art

U.S. Pat. Nos. 5,106,184 and 5,894,337 describe a Doppler fundus blood flow meter that uses the following measurement principle. A blood vessel to be measured is illuminated with measurement light. Two detectors receive from two directions a light beat signal obtained by mixing a scattered light signal, which has been Doppler-shifted by fine particles such as red blood cells contained in blood flowing in the blood vessel, and scattered reference light from a blood vessel wall or surrounding tissue, which has not been Doppler-shifted. These signals undergo FFT (fast Fourier transform) waveform analysis. These references assume as a blood vessel model a so-called Poiseuille flow, which has a maximum blood flow velocity at its center and a lower flow velocity toward the periphery, as shown in FIG. 18. For the two detectors, cutoff frequencies Δfmax1 and Δfmax2 as maximum Doppler shifts corresponding to the maximum blood velocity at the center of the blood vessel are obtained, as shown in FIGS. 19 and 20, and a maximum blood flow velocity is obtained from these values.

It is a common practice to visually determine this cutoff frequency by the operator. APPLIED OPTICS, Vol. 27, No. 6, pp. 1126–1134 (1988) "Retinal laser Doppler velocimetry: toward its computer-assisted clinical use" (B. L. Petrig, C. E. Riva) discloses a method of obtaining the cutoff frequency by assuming an ideal model in which the power spectrum of the FFT waveform vertically drops at a given cutoff frequency. However, the power spectrum of an actual FFT waveform does not have an ideal shape that vertically drops discontinuously, but has a shape that abruptly and continuously drops along a given trend curve. For this reason, it is difficult for the method disclosed in the above reference to accurately discriminate the cutoff frequency.

SUMMARY OF THE INVENTION

The present invention is a challenge to an improvement in the prior art based on the above situation and has as its principal object to provide a Doppler velocimeter which can attain measurement precision higher than the prior art, and can achieve size and cost reductions.

More specifically, it is the first object of the present invention to provide a system which adopts an automated method that can obtain the cutoff frequency with higher precision, and can accurately measure the flow velocity. It is the second object of the present invention to provide a system which can achieve high-precision measurement using a smaller number of detectors than the prior art.

In order to achieve the above objects, one aspect of a Doppler velocimeter according to the present invention comprises an illumination system for illuminating a blood vessel with a light beam, a detector for detecting Doppler-shifted scattered light produced from blood flowing in the blood vessel, and a processor for obtaining a blood flow velocity by analyzing a signal from the detector, wherein the processor compares an actual power spectrum obtained by frequency-analyzing the signal, and a theoretical power spectrum obtained using a frequency as a parameter while changing the parameter.

Other objects and aspects of the present invention will become apparent from the following description of the embodiments.

DETAILED DESCRIPTION OF THE PREFERRED EMBODIMENTS

FIRST EXAMPLE

A fundus blood flow meter that measures the velocity of blood flowing in a blood vessel on the fundus of an eye to be examined will be explained as an example that uses a Doppler velocimeter in blood-flow-velocity measurement.

Note that the application field of the present invention is not limited to such a specific example, but includes a blood flow meter for a blood vessel on the sclera or other blood vessels. Furthermore, the present invention can be applied to a Doppler velocimeter which is useful in every industrial field that requires flow velocity measurement of flood.

Figure 1:
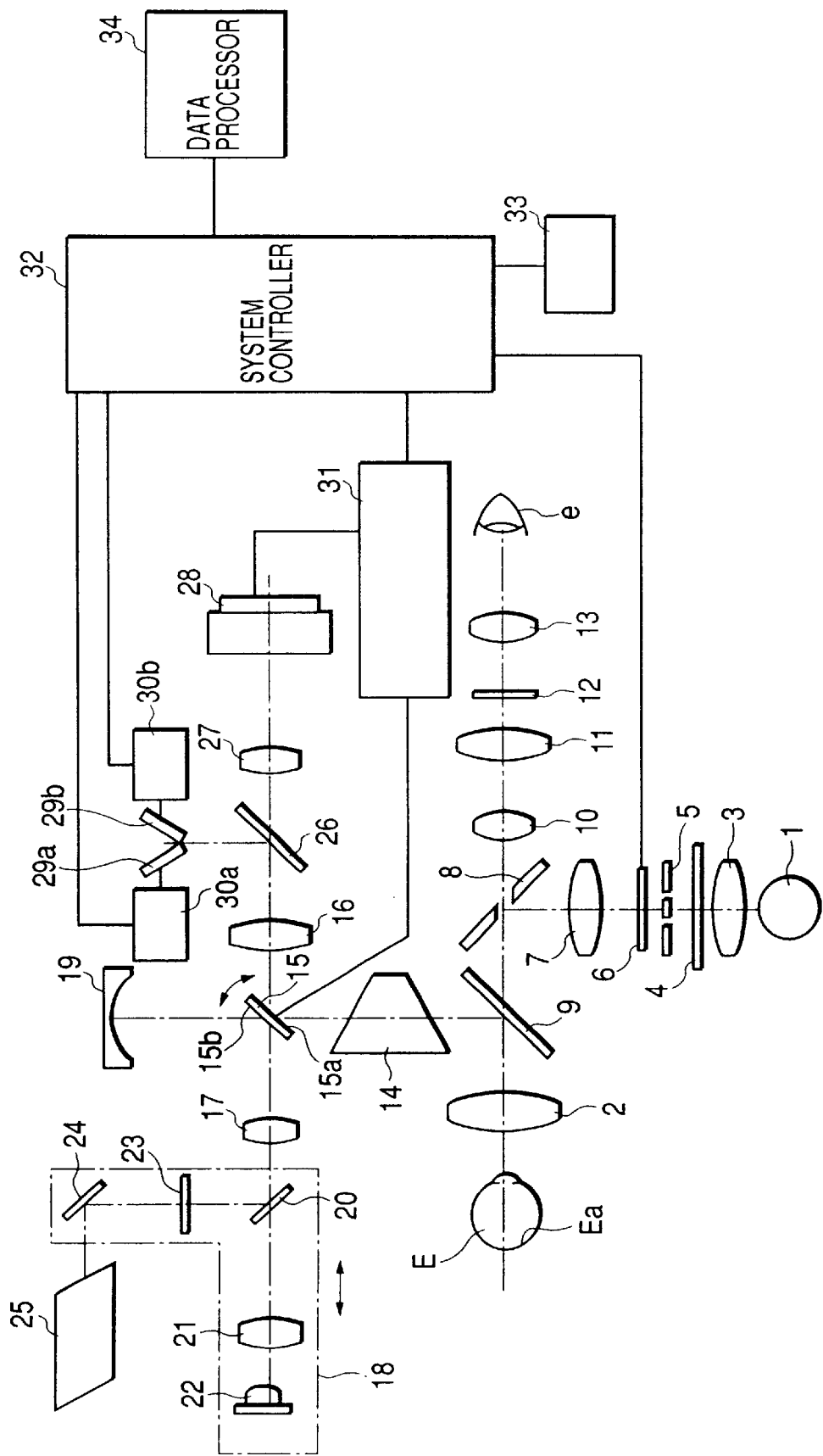
FIG. 1 is a block diagram showing the overall system of a fundus blood flow meter according to the first example of the present invention.

In FIG. 1, a condenser lens 3, a band-pass filter 4 that transmits only wavelength light of, e.g., the yellow range, a ring slit 5 provided at a position nearly conjugate with the pupil of an eye E to be examined, a transmission liquid crystal plate 6 as a fixation target display element, a relay lens 7, an apertured mirror 8, and a band-pass mirror 9 having characteristics for transmitting wavelength light in the yellow range and reflecting most of other light components are disposed in order along an illumination optical path extending from an observation light source 1 comprising, e.g., a tungsten lamp for emitting white light to an objective lens 2 that opposes the eye E to be examined. These members form a fundus illumination optical system. The ring slit 5 is used to separate fundus illumination light and fundus observation light in the anterior segment of the eye E to be examined, and its shape and number are not particularly limited as long as it can form a required light-shielding area. An observation optical system is formed behind the apertured mirror 8, and comprises a focus lens 10 movable along the optical path, a relay lens 11, a scale plate 12, and an eyepiece 13, which are disposed in order along the optical path. The optical path reaches an operator eye e. An image rotator 14 and a galvanometric mirror 15, which has a rotation axis perpendicular to the plane of the page and both its surfaces polished, are disposed along the optical path in the direction of light reflected by the band-pass mirror 9. A second focus lens 16, which is movable along the optical path, is arranged in the direction of light reflected by a lower reflecting surface 15a of the galvanometric mirror 15, and a lens 17 and a focus unit 18, which is movable along the optical axis, are disposed in the direction of light reflected by an upper reflecting surface 15b. The front side focal plane of the lens 17 is conjugate with the pupil of the eye E to be examined, and the galvanometric mirror 15 having an asymmetric shape on the pupil is disposed on that focal plane. A concave mirror 19 is concentrically disposed on the optical axis behind the galvanometric mirror 15 to constitute a relay optical system for imaging the upper and lower reflecting surfaces 15b and 15a of the galvanometric mirror 15 at −1x, so that a laser beam reflected by the upper reflecting surface 15b of the galvanometric mirror 15 passes through a notch of the galvanometric mirror 15. In the focus unit 18, a dichroic mirror 20, a focusing lens 21, and a measurement light source 22 such as a laser diode or the like for generating a light beam are disposed in order on the same optical path as that of the lens 17, and a mask 23 and mirror 24 are disposed on the optical path of light reflected by the dichroic mirror 20, and the focus unit 18 bounded by the dotted line is integrally movable in the directions of arrows. Furthermore, a tracking light source 25 for emitting high-luminance light, e.g., green light, which is different from light from other light sources, is disposed on the optical path of light incident on the mirror 24. On the optical path of light reflected by the lower reflecting mirror 15a of the galvanometric mirror 15, a dichroic mirror 26, a magnifying lens 27, and a two-dimensional image sensing element 28 with an image intensifier are disposed in order behind the second focus lens 16 so as to construct a blood-vessel detection system. On the optical path of light reflected by the dichroic mirror 26, two mirrors 29a and 29b that form an entrance pupil by circular reflecting surfaces, and two photomultipliers 30a and 30b as photodetectors are disposed to construct a measurement optical system. Note that all the optical paths are illustrated on an identical plane for the sake of illustrative convenience, but the mirrors 29a and 29b and photomultipliers 30a and 30b are disposed in a direction perpendicular to the plane of the page. The detector is not limited to a photomultiplier, and a semiconductor sensor with high sensitivity or the like can be used. The output from the two-dimensional image sensing element 28 is connected to a tracking controller 31, the output of which is connected to the galvanometric mirror 15, and also to a system controller 32 for controlling the overall apparatus. The photomultipliers 30a and 30b and an operation console 33 are connected to the system controller 32. The system controller 32 is connected to a data processor 34.

White light emitted by the observation light source 1 is transmitted through the condenser lens 3, and only yellow wavelength light is transmitted through the band-pass filter 4. A light beam that has passed through the ring slit 5 illuminates the transmission liquid crystal plate 6 from behind, and is reflected by the apertured mirror 8 via the relay lens 7 After that, only yellow wavelength light is transmitted through the band-pass mirror 9, temporarily forms a ring slit image on the pupil of the eye E to be examined via the objective lens 2, and then nearly evenly illuminates a fundus Ea of the eye. At this time, a fixation target is displayed on the transmission liquid crystal plate 6, is projected onto the fundus Ea of the eye E to be examined by illumination light, and is presented to the eye E to be examined as a fixation target image. Light reflected by the fundus Ea of the eye returns along the same optical path, and is picked up as a fundus observation light beam from the position above the pupil. The light beam passes through the central aperture of the apertured mirror 8, the focus lens 10, and the relay lens 11, forms a fundus image on the scale plate 12, and is then observed by the operator's eye e via the eyepiece 13. The operator can align the apparatus while observing this fundus image. Measurement light as a light beam emitted by the measurement light source 22 is transmitted through an upper decentered portion of the focusing lens 21, and is then transmitted through the dichroic mirror 20. On the other hand, tracking light emitted by the tracking light source 25 is reflected by the mirror 24, and is then shaped into a desired shape by the mask 23. Furthermore, the tracking light is reflected by the dichroic mirror 20, and is superposed on the measurement light that forms a spot at a position conjugate with the center of the aperture of the mask 23. The measurement light and tracking light are transmitted through the lens 17, are temporarily reflected by the upper reflecting surface 15b of the galvanometric mirror 15, are further reflected by the concave mirror 19, and then return toward the galvanometric mirror 15. Due to the function of the relay optical system, the two light beams reflected by the upper reflecting surface 15b of the galvanometric mirror 15 return to the position of the notch of the galvanometric mirror 15, and travel toward the image rotator 14 without being reflected by the galvanometric mirror 15. The two light beams which have been deflected in the direction of the objective lens 2 by the band-pass mirror 9 via the image rotator 14 hit the fundus Ea of the eye E to be examined via the objective lens 2. At this time, the tracking light is shaped to have a size of around 300 to 500 $\mu$m in a direction in which the blood vessel runs and a size of around 500 to 1,200 $\mu$m in a direction perpendicular to that in which the blood vessel runs. On the other hand, the measurement light is shaped into a circular spot of 50 to 120 $\mu$m as large as the blood vessel to be measured or an elliptic shape having a longitudinal direction in the direction in which the blood vessel runs. Scattered reflected light at the fundus Ea is focused again by the objective lens 2, is reflected by the band-pass mirror 9, and is transmitted through the image rotator 14. The light is reflected by the lower reflecting surface 15a of the galvanometric mirror 15, and strikes the dichroic mirror 26 via the focus lens 16 to be separated into the measurement light and tracking light. The tracking light is transmitted through the dichroic mirror 26 and forms on the two-dimensional image sensing element 28 a blood vessel image magnified by the magnifying lens 27 to be larger than the fundus image formed by the observation optical system. The image sensing range at that time is nearly equal to the illumination range of the tracking light. This blood vessel image signal is input to the tracking controller 31, and is converted into a blood vessel position signal. The tracking controller 31 controls the rotational angle of the galvanometric mirror 15 using this signal to track the blood vessel. Some light components of the measurement light and tracking light scattered and reflected by the fundus Ea are transmitted through the band-pass mirror 9, and are guided to the observation optical system behind the apertured mirror 8. The tracking light then forms a rod-like indicator on the scale plate 12, and the measurement light forms a spot image at the central portion of this indicator. These images are observed together with the fundus image Ea' and fixation target image via the eyepiece 13. At this time, the spot image of the measurement beam superposed at the center of the indicator is observed. The indicator can linearly move on the fundus Ea by rotating the galvanometric mirror 15 using the operation console 33.

Upon measurement, the operator makes focus adjustment of the fundus image. When the operator adjusts a focus knob at the operation console 33, the transmission liquid crystal plate 6, focus lenses 10 and 16, and focus unit 18 move together by actuators along the optical path. When the fundus image is in focus, the transmission liquid crystal plate 6, the scale plate 12, and the two-dimensional image sensing element 28 simultaneously become conjugate with the fundus Ea. After the operator adjusts the focus to the fundus image, he or she operates the operation console 33 to change the observation region by guiding the fixation of the eye E to be examined, and to move the blood vessel to be measured to an appropriate position. Based on this operation, the system controller 32 controls the transmission liquid crystal plate 6 to move the fixation target image on the screen, and rotates the image rotator 14 to make the line that connects the optical axis of the fundus blood flow meter and the center of each photomultiplier 30 parallel to the direction in which the blood vessel to be measured runs. At this time, the direction perpendicular to the pixel array of the two-dimensional image sensing element and the moving direction of the measurement beam upon rotation of the galvanometric mirror are simultaneously adjusted to a direction perpendicular to the direction in which the blood vessel runs. The operator starts tracking, checks the tracking, and then starts measurement by pressing a measurement switch at the operation console 33. During the measurement period, the measurement beam is automatically held on the blood vessel upon operation of the tracking controller 31. The measurement light scattered and reflected by the blood vessel is reflected by the dichroic mirror 26, and is detected by the two photomultipliers 30a and 30b via the two mirrors 29a and 29b. The output signals from these photomultipliers undergo frequency analysis such as an FFT process or the like in the system controller 32. The FFT waveform obtained by such process is analyzed by the data processor 34 to compute the blood flow velocity at the fundus Ea.

Figure 2:
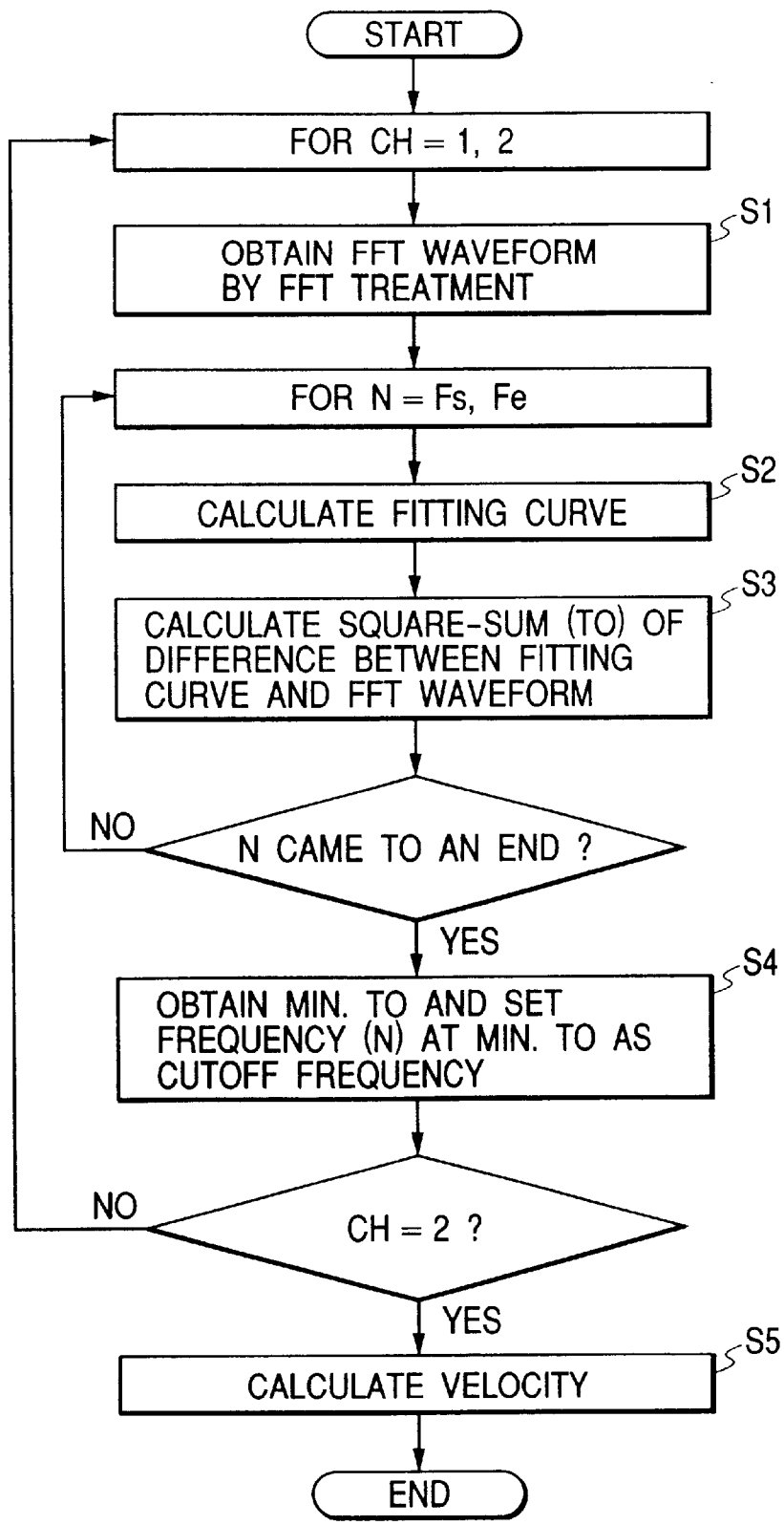
FIG. 2 is a flow chart showing the data processing sequence of the first example.

FIG. 2 is a flow chart showing the process in the data processor 34. This flow chart roughly has steps S1 to S5. Using a frequency N as a parameter, steps S2 and S3 are repeated while increasing N little by little so as to implement a fitting process. This process is done for the signals (CH1, CH2) from the two photomultipliers.

In step S1, the signal from one photomultiplier is frequency-analyzed by the FFT process. Furthermore, the obtained FFT waveform is smoothed to obtain a smooth power spectrum curve.

In step S2, a theoretical fitting curve is computed. Using the practical range from Fs to Fe (0 to 50 kHz in this example) of the frequency N as a parameter, a fitting curve as a model shape of the FFT waveform is obtained while changing the parameter little by little.

Figure 3:
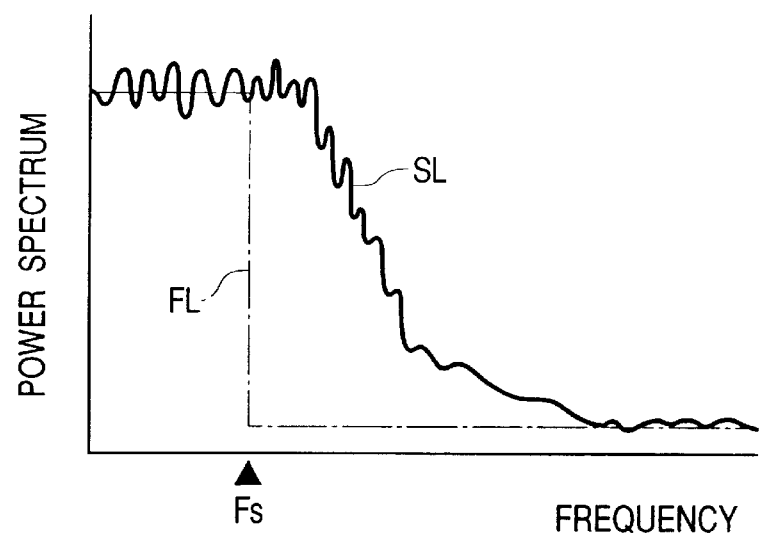
FIG. 3 is a graph of a fitting curve assuming that the entrance pupil is a point.

Assuming that the entrance pupil A is an infinitesimal point, an ideal model of the FFT waveform has a shape in which the power spectrum discontinuously and vertically drops at a frequency Fs, as indicated by the broken curve FL in FIG. 3. However, in practice, the entrance pupil A is not a point but has a specific shape (e.g., circle or ellipse) having a given area (or size). For this reason, the FFT waveform does not have a shape like FL, but has a shape that gradually drops along a certain trend curve, as indicated by the solid curve SL.

Figure 4:
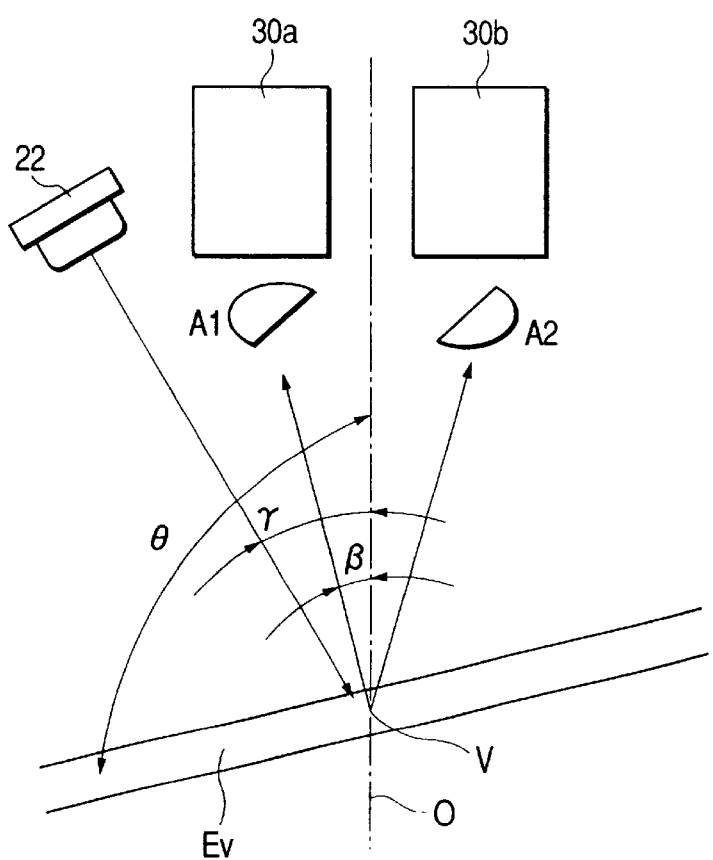
FIG. 4 is an explanatory view of the relationship among a portion to be measured, a measurement light source, a photomultiplier, and an entrance pupil.

FIG. 4 shows the relationship among a portion V to be measured of the blood vessel Ev to be measured, the measurement light source 22, the photomultipliers 30a and 30b, and entrance pupils A1 and A2 formed by the mirrors 29a and 29b. Note that this example uses a mirror as an optical element that forms the entrance pupil of a detector. Alternatively, as other equivalent means, an aperture stop may be used, an optical fiber may be used to form an entrance pupil at its incident end, or the light-receiving unit of the photomultiplier may have a size and shape to substantially have the entrance pupil A. The detector is not limited to the photomultiplier, and a semiconductor sensor with high sensitivity or the like may be used. The same applies to other examples.

In FIG. 4, let θ be the angle the optical axis O of the fundus blood flow meter makes with the direction in which the blood vessel Ev to be measured runs, let γ be the angle the optical axis O makes with the direction of incidence of the measurement light source 22 to the portion V to be measured, and let β be the angle the optical axis O makes with the light-receiving direction from the portion V to be measured to the entrance pupils A1 and A2. A cutoff frequency Δf of an FFT of each beat signal received by the photomultiplier 30a or 30b, and the angles θ, γ, and β satisfy:

$$\Delta f \propto \cos(\theta-\beta)+\cos(\theta-\gamma) \quad (1)$$

Note that these angles θ, γ, and β use values converted into angles in the human eye.

Figure 5:
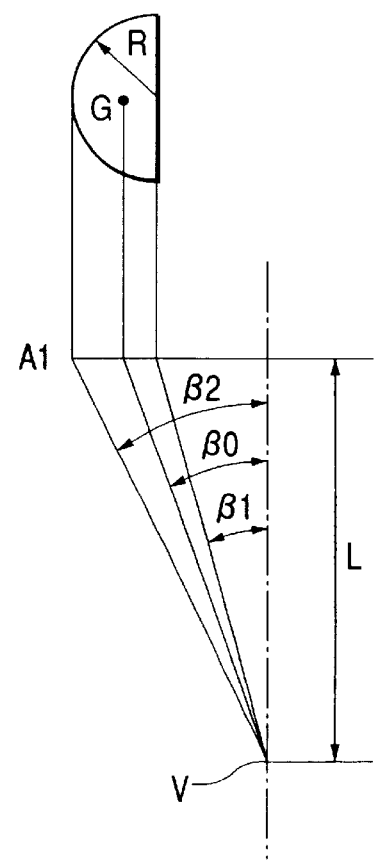
FIG. 5 is an explanatory view of the positional relationship of the entrance pupil.

FIG. 5 is a plan view showing the positional relationship of one entrance pupil A1. In this example, the semicircular mirrors 29a and 29b are used to form semicircular entrance pupils A1 and A2 with a radius R, and information that pertains to the shape of these entrance pupils A1 and A2 is stored in the system controller 32. More specifically, the information includes the distance between the centers of the two semicircles, the radius, and the like, and is not particularly limited, as long as the relationship between the angle β and the area is known. Such information is stored in the form of a formula or correspondence table. A power spectrum P of an FFT of a beat signal formed from a small portion with the angle β in the entrance pupil A1 is proportional to the area of that small portion and satisfies:

$$P \propto [R^2 - \{L(\tan\beta - \tan\beta 1)\}^2]^{1/2} \quad (2).$$

The FFT of the beat signal formed from the right portion of the entrance pupil A1 has a lower frequency and larger power spectrum P than the FFT of the beat signal formed from the left portion. The power spectrum P of the FFT of the beat signal formed by the entire entrance pupil A1 is obtained by superposing power spectra P in the range from angles β1 to β2 in FIG. 5, and the shape of the trend curve in which the power spectrum P of the FFT waveform continuously drops near the cutoff frequency, i.e., a theoretical cutoff shape, can be obtained. Basically, the slope of the curve becomes slower with the increasing size (area) of the entrance pupil (i.e., with the increasing range from β1 to β2). Note that the theoretical cutoff shape is computed as needed. Alternatively, numerical values of the theoretical cutoff shapes computed in advance may be pre-stored in a memory of the system controller 32 or a storage medium, such as a storage disk or the like, and data may be read out as needed. In this example, Δfmax1 represents the cutoff frequency based on an angle β0 within the range from the angles β1 to β2, the optical axis O makes with the center G of gravity of the entrance pupil A1 from the portion V to be measured, and a computation is made by the method to be described below.

Figure 6:
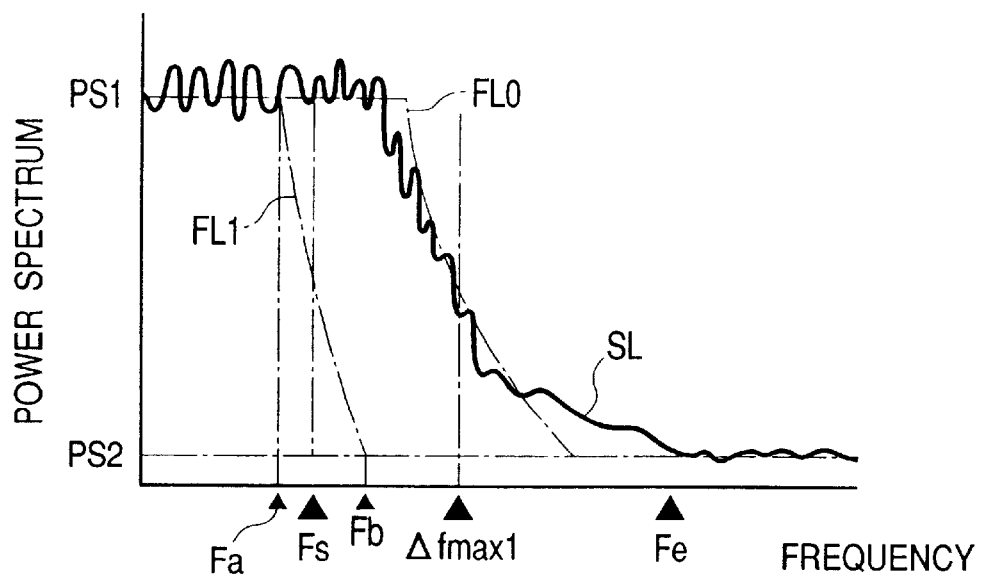
FIG. 6 is a graph for explaining an example of the method of computing a fitting curve.

FIG. 6 is a graph for explaining an example of the method of computing a fitting curve. The broken curve FL1 represents the fitting curve obtained by computation when the angle θ the optical axis O makes with the direction in which the blood vessel Ev to be measured runs is 90°, and a frequency Fs is assumed to be a temporary cutoff frequency to fit the frequency analysis result of the output signal. If Fa represents the frequency at which the theoretical cutoff shape begins to drop, a power spectrum PS1 in the range lower than the frequency Fa uses the average value of the power spectrum P lower than the frequency Fa of the actual FFT waveform indicated by the solid curve SL. On the other hand, if Fb represents the frequency at the terminal end of the theoretical cutoff frequency, a power spectrum PS2 in the range higher than the frequency Fb uses the average value of noise components having a sufficiently high frequency of the actual FFT waveform. Since a method of obtaining these average values can be implemented by simple computations, computations can be made within a short period of time. In this manner, a fitting curve is generated by superposing PS2 as noise components on the theoretical cutoff shape so that the terminal end of the theoretical cutoff shape has PS2, and enlarging/reducing the curve so that the height of the theoretical cutoff shape is (PS1–PS2). The cutoff frequency portion of this fitting curve has a shape approximate to that of the actual FFT waveform, and the cutoff frequency can be obtained with high precision, thus accurately obtaining the blood flow velocity.

Figure 7:
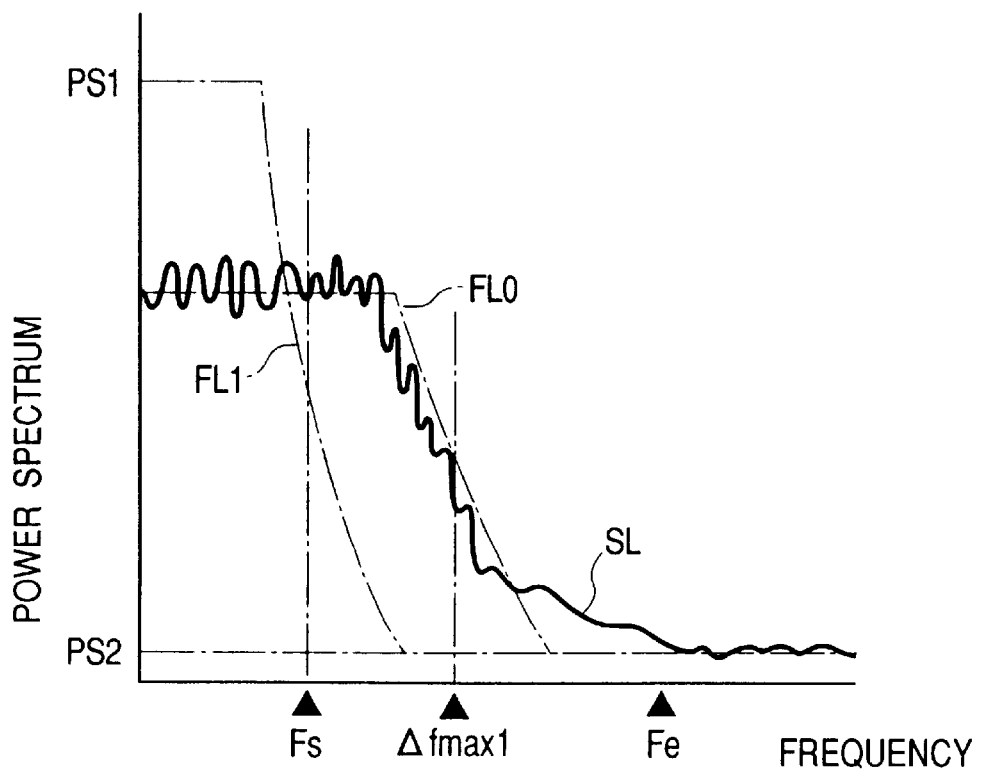
FIG. 7 is a graph showing a fitting curve obtained by another method.

FIG. 7 shows another method of obtaining a fitting curve. The curve portion of the theoretical cutoff shape and the power spectrum PS2 within the range higher than frequency Fb are obtained in the same manner as in FIG. 6, but the power spectrum PS1 within the range lower than the frequency Fa is obtained by a different method. A value obtained by integrating a portion obtained by subtracting the power spectrum PS2, considered as noise components, from the power spectrum P of the actual FFT waveform indicated by the solid curve SL over the entire frequency range, and a value obtained by integrating a portion obtained by subtracting the power spectrum PS2 from the power spectrum P of the fitting curve within the range lower than the frequency Fb, are considered. Then, the power spectrum PS1 that can make the considered values equal to each other, i.e., that can equalize the total of power spectra P, is determined. In this case, if temporary cutoff frequency Fs is far from the cutoff frequency of the actual FFT waveform, the shape of the fitting curve is largely different from the actual FFT waveform, but the shape of the fitting curve becomes closer to the actual FFT waveform toward the actual cutoff frequency. FL0 indicates the fitting curve that best fits the actual FFT power spectrum. With this method, convergence can improve upon a comparison to be described later, and the cutoff frequency can be obtained with higher precision.

Referring back to FIG. 2, the theoretical fitting curve obtained as described above is compared with the actual FFT waveform in step S3. As an example of the comparison, the differences between the power spectrum values of the fitting curve and FFT waveform are obtained along the frequency axis, and their square sum $T_0$ is computed. Note that the comparison algorithm is not limited to such a specific one, but various other algorithms may be used. For example, a division may be used in place of a subtraction, or the sum of the absolute values of the differences may be computed without squaring the differences. The same applies to examples to be described later.

The square sum $T_0$ of the differences between the values of the fitting curve obtained as described above and the actual FFT waveform is computed by increasing the frequency in given increments within the range from Fs to Fe, and steps S2 and S3 are repeated for each frequency. When this process is repeated until the final frequency Fe, the square sum values $T_0$ having the frequency as a parameter can be obtained. After that, a minimum one of a large number of square sums $T_0$ obtained as described above is obtained in step S4. When $T_0$ is a minimum, i.e., when it is determined as a result of comparison that the fitting curve and the actual FFT waveform best fit (close to each other), the frequency N is determined to be a cutoff frequency Δfmax1. The theoretical fitting curve at that time has a shape closest to the actual FFT waveform, as indicated by the solid curve FL0 in FIG. 6, and the cutoff frequency as information that reflects the maximum blood flow velocity can be obtained with high precision.

Likewise, the processes in steps S1 to S4 are done for the output signal (CH2) from the other photomultiplier to obtain the cutoff frequency Δfmax2. In step S5, the maximum blood flow velocity Vmax is computed using the two values by:

$$\text{Vmax} = \{\lambda/(n\cdot\alpha)\}\cdot|\Delta fmax1 - \Delta fmax2| \quad (3)$$

where λ is the wavelength of the measurement light beam, n is the refractive index of the portion to be measured, and α is the angle the two light-receiving optical axes in the eye make.

With the aforementioned sequence, a precise cutoff frequency can be automatically obtained, and the maximum blood flow velocity Vmax can be obtained with high precision.

According to this example, the cutoff frequency is obtained by comparing the actual power spectrum obtained by frequency-analyzing the signal from the detector, and the theoretical power spectrum that is obtained using the frequency as a parameter and has a curve with a slope that reflects the shape or size of the pupil, while changing the parameter.

SECOND EXAMPLE

A fundus blood flow meter according to the second example will be explained below using FIG. 8. The arrangement of the overall system is similar to that shown in FIG. 1, and the same reference numerals denote the same members. The differences from the first example reside in the use of only one detector for receiving scattered light and the algorithm for computing the blood flow.

Figure 8:
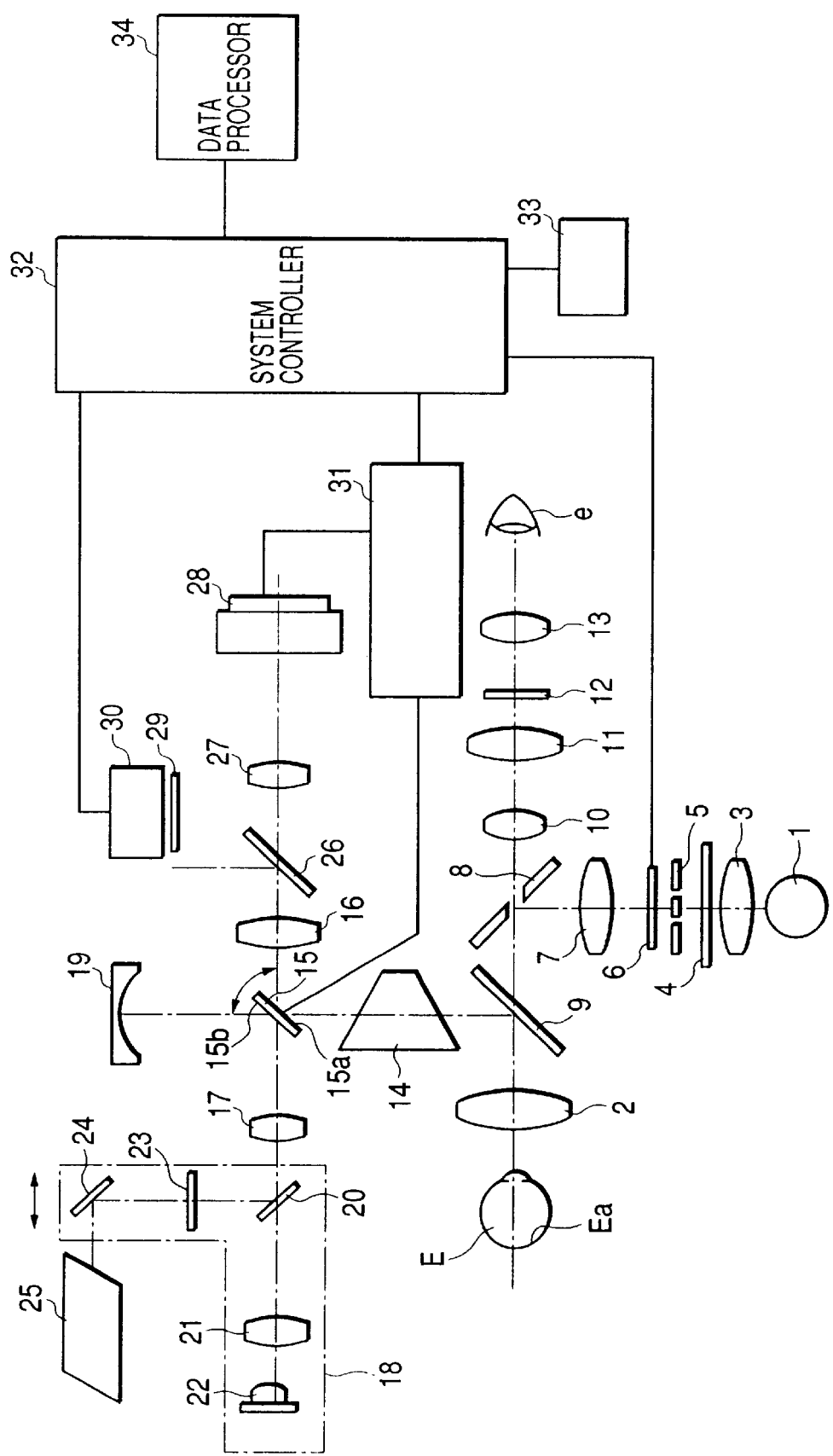
FIG. 8 is a block diagram showing the overall system of a fundus blood flow meter according to the second example of the present invention.

Referring to FIG. 8, an aperture stop 29 that forms an entrance pupil by a circular aperture, and a single photomultiplier 30 serving as a photodetector are disposed on the optical path of light reflected by the dichroic mirror 26 to construct the measurement optical system.

Figure 10:
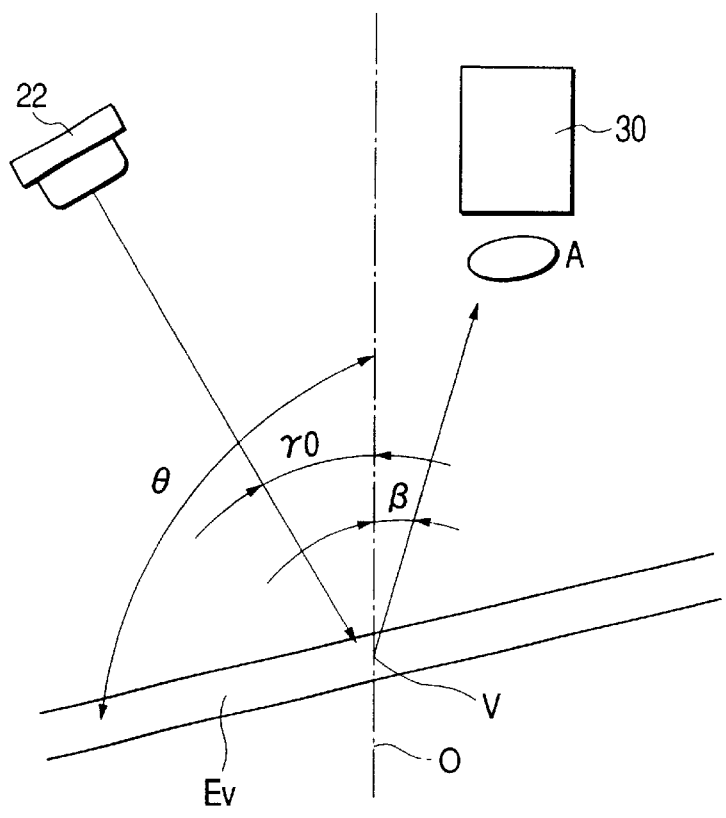
FIG. 10 is an explanatory view of the relationship among a portion to be measured, a measurement light source, a photomultiplier, and an entrance pupil.
Figure 11:
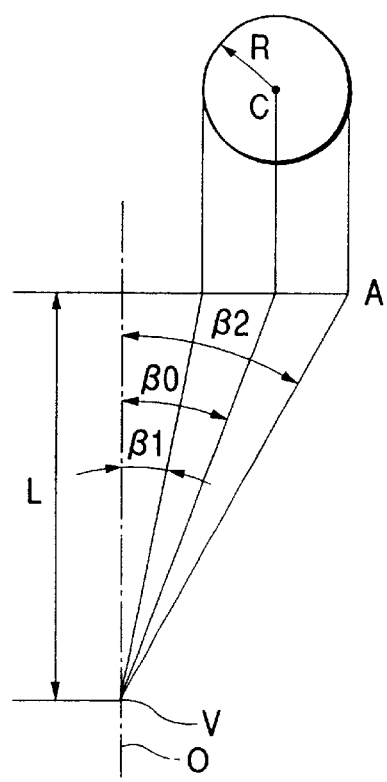
FIG. 11 is an explanatory view of the positional relationship of the entrance pupil.

FIG. 10 shows the relationship among the portion V to be measured of the blood vessel Ev to be measured, a measurement light source 22, a photomultiplier 30, and an entrance pupil A formed by the aperture stop 29. Let Θ be the blood vessel angle the optical axis O (reference axis of the apparatus) as the apparatus reference of the fundus blood flow meter makes with the direction in which the blood vessel Ev to be measured runs, let $\gamma_0$ be the incident angle the optical axis O makes with the direction of light incident on the portion V to be measured, and let β be the light-receiving angle the optical axis O makes with the light-receiving direction from the portion V to be measured to the entrance pupil A. From another point of view, the blood vessel angle θ is information indicating the direction of the blood vessel Ev with reference to the apparatus. On the other hand, FIG. 11 is a plan view showing the positional relationship of the entrance pupil A. The entrance pupil A has a circular shape with a radius R, and $\beta_0$ is the light-receiving angle of a center C of the entrance pupil A. The blood vessel angle θ in FIG. 10 is a parameter that differs depending on the direction the blood vessel Ev runs, and the light-receiving angle β in FIG. 10 is a parameter which differs depending on the light-receiving direction within the angle range from β1 to β2 in FIG. 11. Note that these angles θ, $\gamma_0$, β use values converted into those in the human eye.

Figure 9:
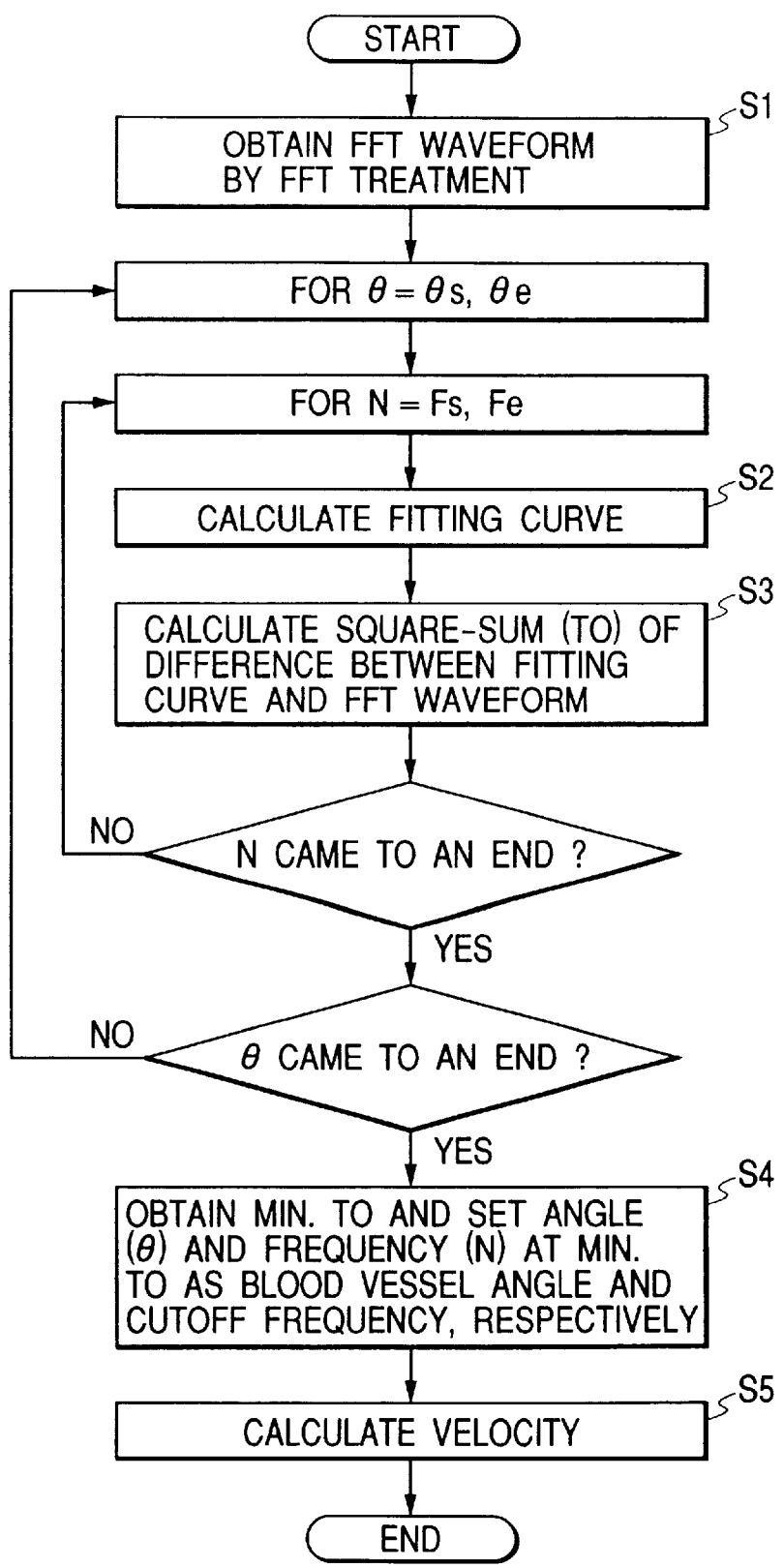
FIG. 9 is a flow chart showing the data processing sequence of the second example.

FIG. 9 is a flow chart showing the process having steps 1 to 5 in the data processor 34. Using θ and N as parameters, steps S2 and S3 are repeated while changing these parameters little by little, so as to implement the fitting process.

In step S1, the signal from the photomultiplier 30 is frequency-analyzed by the FFT process. Furthermore, the obtained FFT waveform is smoothed to obtain a smooth power spectrum curve.

In step S2, a theoretical fitting curve is computed. An angle range from θs to θe (75° to 105° in this example) that can be assumed in practice is used as the first parameter, and the range from Fs to Fe (0 to 50 kHz in this example) of practical frequency N is used as the second parameter. While changing the two parameters little by little in double loops, a fitting curve as a model shape of the FFT waveform is obtained.

Figure 12:
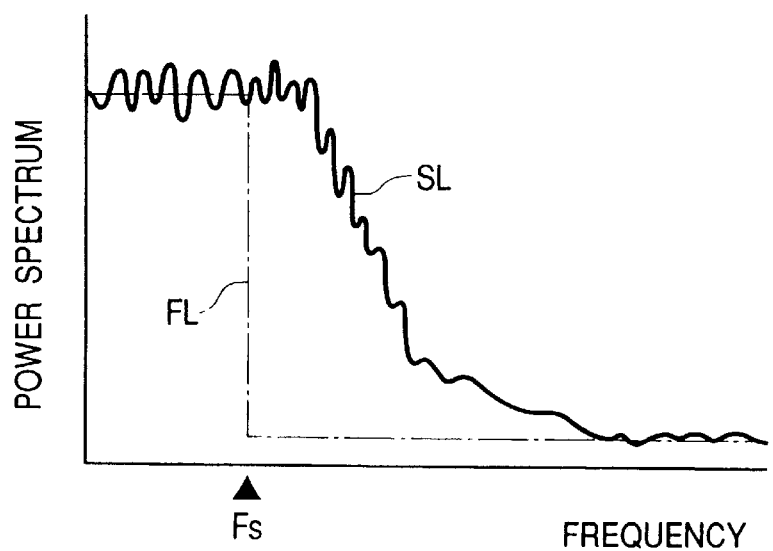
FIG. 12 is a graph of a fitting curve assuming that the entrance pupil is a point.

Assuming that the entrance pupil A is an infinitesimal point, an ideal model of the FFT waveform has a shape in which the power spectrum discontinuously drops at the frequency Fs, as indicated by the broken curve FL in FIG. 12. However, in practice, the entrance pupil A is not a point but has a specific shape (e.g., circle or ellipse) having a given area (or size). For this reason, the FFT waveform does not have a shape like FL, but has a shape that gradually drops along a certain trend curve, as indicated by the solid curve SL.

Of the light beat signal detected by the photomultiplier 30, a cutoff frequency Δf of an FFT due to a light beat signal in the light-receiving direction of the light-receiving angle β can be defined using a cutoff frequency $\Delta f_0$ at the light-receiving angle $\beta_0$, and the angles θ, $\gamma_0$, β, and $\beta_0$ by:

$$\Delta f = \Delta f_0 \cdot |\{\cos(\theta+\beta)+\cos(\theta-\gamma_0)\}/\{\cos(\theta+\beta_0)+\cos(\theta-\gamma_0)\}| \quad (4)$$

The power spectrum P of an FFT of a light beat signal formed by a portion of the light-receiving angle β in the entrance pupil is proportional to the area of that portion, and satisfies:

$$P \propto [R^2 - \{L(\tan\beta - \tan\beta_0)\}^2]^{1/2} \quad (5)$$

where L is the distance between the plane formed by the entrance pupil A, and the portion V to be measured.

The power spectrum P of the FFT of the light beat signal formed by the entire circular entrance pupil A having the predetermined area is obtained by superposing power spectra within the range from the light-receiving angles β1 to β2 shown in FIG. 11. Based on this recognition, the shape of a curve (theoretical cutoff shape) in which the power spectrum P of the FFT waveform continuously drops with a given slope near the cutoff frequency is obtained. Basically, the slope of the curve becomes slower with the increasing size (area) of the entrance pupil (i.e., with the increasing range from β1 to β2). The theoretical cutoff shape is computed as needed, or numerical values of the theoretical cutoff shapes computed in advance are pre-stored in a memory of the system controller 32 or a storage medium, such as a storage disk or the like.

Figure 13:
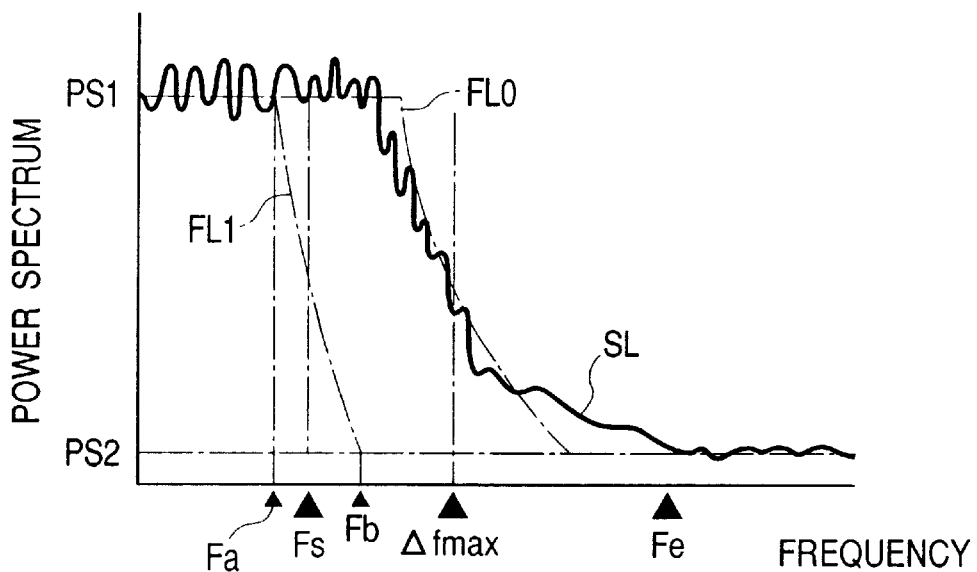
FIG. 13 is a graph of a fitting curve in consideration of the influence of the area of the entrance pupil.

FIG. 13 is a graph for explaining an example of the method of obtaining a fitting curve. The broken curve FL1 represents the fitting curve computed when the blood vessel angle θ=θs and the cutoff frequency N=Fs. If Fa represents the frequency at which the theoretical cutoff shape begins to drop, a power spectrum PS1 in the range lower than the frequency Fa is the average value of the power spectrum P of the actual FFT waveform that includes a fine periodic waveform, as indicated by the solid curve SL. On the other hand, if Fb represents the frequency at the terminal end of the theoretical cutoff frequency, a power spectrum PS2 in the range higher than the frequency Fb is the average value of the range sufficiently high frequency range (frequency higher than Fe) of the actual FFT waveform. Since the sufficiently high frequency range includes only noise components, PS2 can be the average value of noise components. Since computations for obtaining the average values are simple, the load on the data processor is small, and computations can be made within a short period of time. In this manner, a fitting curve is generated by superposing PS2 as noise components on the theoretical cutoff shape so that the terminal end of the theoretical cutoff shape has PS2, and enlarging/reducing the entire height so that the height of the theoretical cutoff shape becomes equal to (PS1–PS2). FL0 represents the fitting curve which best fits the actual FFT power spectrum.

Figure 14:
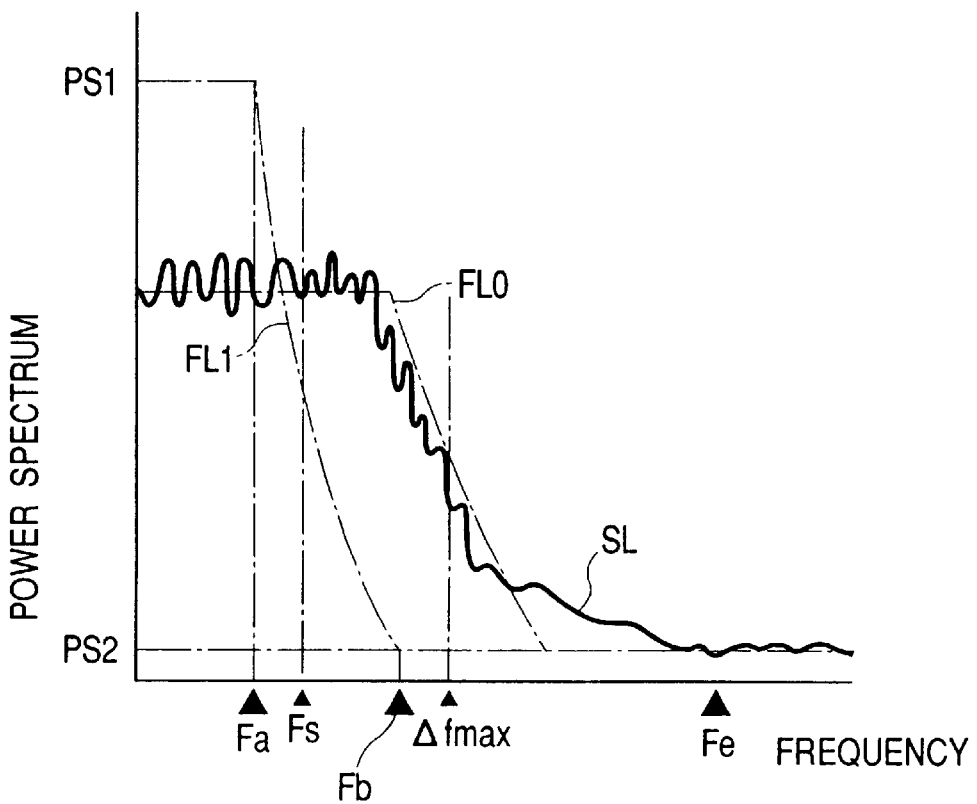
FIG. 14 is a graph showing a fitting curve obtained by another method.

FIG. 14 shows another method of obtaining a fitting curve. The curve portion of the theoretical cutoff shape and the power spectrum PS2 within the range higher than frequency Fb are obtained in the same manner as in FIG. 13, but the power spectrum PS1 within the range lower than the frequency Fa is obtained by a different method A value obtained by integrating a portion obtained by subtracting the power spectrum PS2, considered as noise components, from the power spectrum P of the actual FFT waveform, indicated by the solid curve SL over the entire frequency range, and a value obtained by integrating a portion obtained by subtracting the power spectrum PS2 from the power spectrum P of the fitting curve within the range lower than the frequency Fb, are considered. Then, the power spectrum PS1 that can make the considered values equal to each other, i.e., that can equalize the total of power spectra P, is determined. In this case, if temporary cutoff frequency Fs is far from the cutoff frequency of the actual FFT waveform, the shape of the fitting curve is largely different from the actual FFT waveform, but the shape of the fitting curve becomes closer to the actual FFT waveform toward the actual cutoff frequency. FL0 indicates the fitting curve that best fits the actual FFT power spectrum. With this method, convergence can improve upon comparison to be described later, and the cutoff frequency can be obtained with higher precision.

In step S3 in FIG. 9, the theoretical fitting curve obtained as described above is compared with the actual FFT waveform. As an example of the comparison, the differences between the power spectrum values of the fitting curve and the FFT waveform are obtained along the frequency axis, and their square sum $T_0$ is computed.

By executing the loop process of steps S2 and S3 while increasing the frequency N from Fs to Fe in predetermined increments, fitting for frequency is done. In its outer loop, by repetitively changing the blood vessel angle θ from θs to θe at given steps, fitting for the blood vessel angle θ is done. Finally, a large number of comparison results (values of square sums $T_0$) having the blood vessel angle θ and frequency N as parameters are obtained.

In step S4 in FIG. 9, a minimum one of a large number of square sums $T_0$ obtained as described above is obtained. When $T_0$ is a minimum, i.e., when it is determined as a result of comparison that the fitting curve and the actual FFT waveform best fit, the blood vessel angle θ at that time is determined to be a blood vessel angle θv of the portion V to be measured, and the frequency N at that time is determined to be a cutoff frequency Δfmax at the light-receiving angle $β_0$. The theoretical fitting curve at that time has a shape closest to the actual FFT waveform, as indicated by the solid curve FL0 in FIG. 6, and the cutoff frequency as information that reflects the maximum blood flow velocity can be obtained with high precision. The blood vessel angle θv is information that reflects the direction of the blood vessel with reference to the apparatus, and the accurate blood flow velocity can be obtained by the following computation irrespective of the direction of the blood vessel.

Finally, in step S5 in FIG. 9 a maximum blood flow velocity Vmax is computed by:

$$Vmax=λ·Δfmax/\{n|\cos(θv+β_0)+\cos(θv-γ_0)|\} \qquad (6)$$

where γ is the wavelength of the measurement light beam, and n is the refractive index of the portion to be measured.

In steps S1 to S5 mentioned above, even when a single detector is used, the cutoff frequency can be obtained automatically, and the maximum blood flow velocity Vmax can be obtained with high precision irrespective of the direction of the blood vessel.

If detection signals are obtained with a sufficiently high S/N ratio even when two or more detectors are disposed, since two maximum blood flow velocities that become equal to each other are obtained by executing the aforementioned fitting processes for the individual detection signals in terms of the blood vessel angle and frequency, the maximum blood flow velocity can be obtained with higher precision by averaging them.

As described above, according to this example, the cutoff frequency and the information indicating the direction of the blood vessel are obtained by comparing the power spectrum, which is obtained by frequency-analyzing the signal from the detector, and the theoretical power spectrum obtained using the frequency and the direction of the blood vessel with reference to the apparatus. Since the blood flow velocity is computed using them, high-precision measurement can be implemented if the number of detectors is reduced. Even when an expensive photomultiplier is used as the detector, since the number of detectors used can be reduced to 1, cost and size reductions of the apparatus can be achieved at the same time.

THIRD EXAMPLE

A fundus blood flow meter according to the third example will be explained below. Since the overall system of this example, especially, the optical system, is the same as that shown in FIG. 1, a description of the arrangement will be omitted. The difference from the first example resides in the algorithm for computing the blood flow. When the outputs from the two detectors undergo computations in the sequence explained in <SECOND EXAMPLE> above, more pieces of information are obtained to improve measurement reliability.

Figure 15:
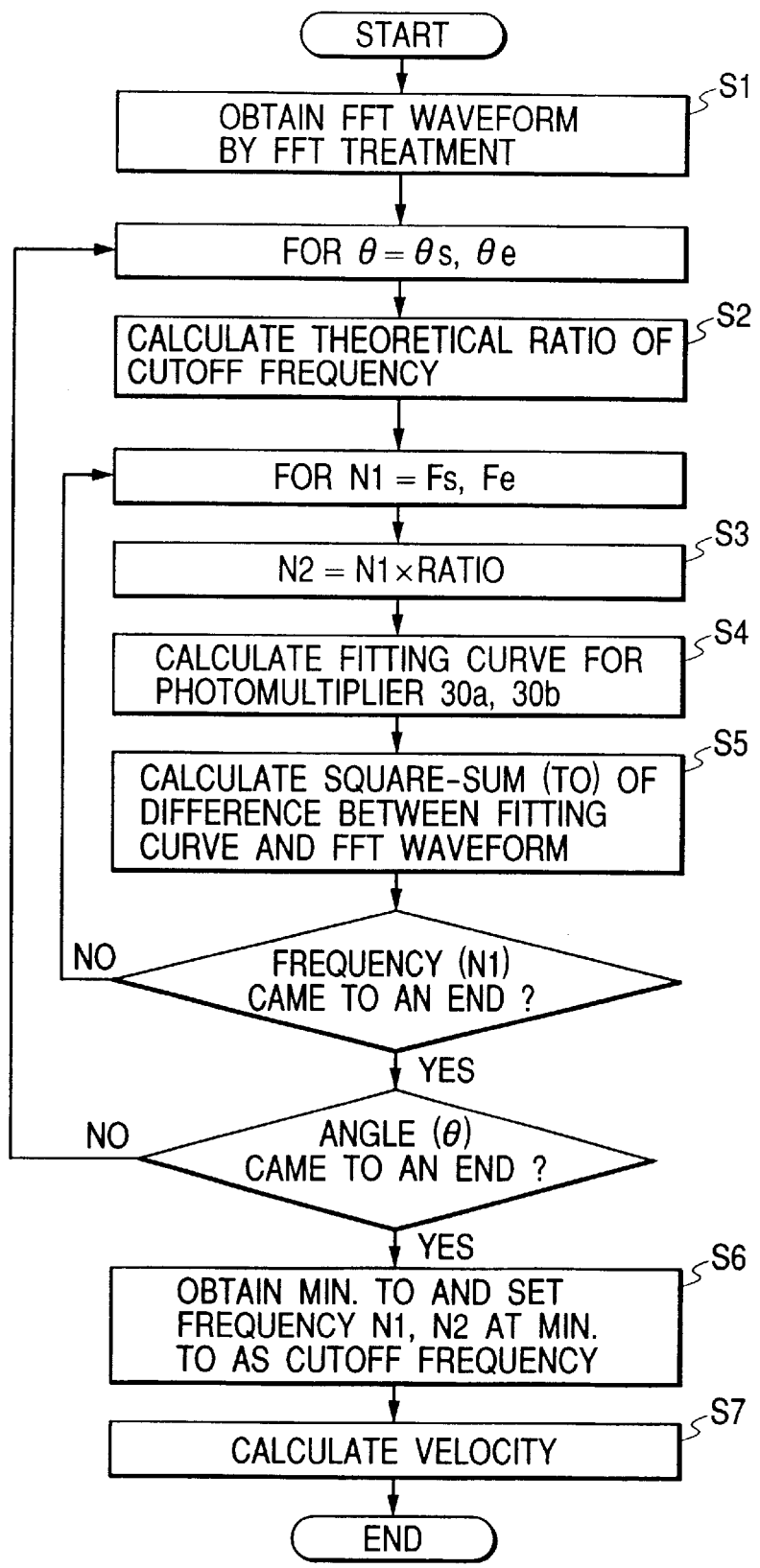
FIG. 15 is a flow chart showing the data processing sequence according to the third example of the present invention.

FIG. 15 is a flow chart showing the operation of the data processor 34. In step S1, FFT waveforms obtained by executing FFT processes of the signals from the photomultipliers 30a and 30b undergo processes such as smoothing and the like.

Figure 16:
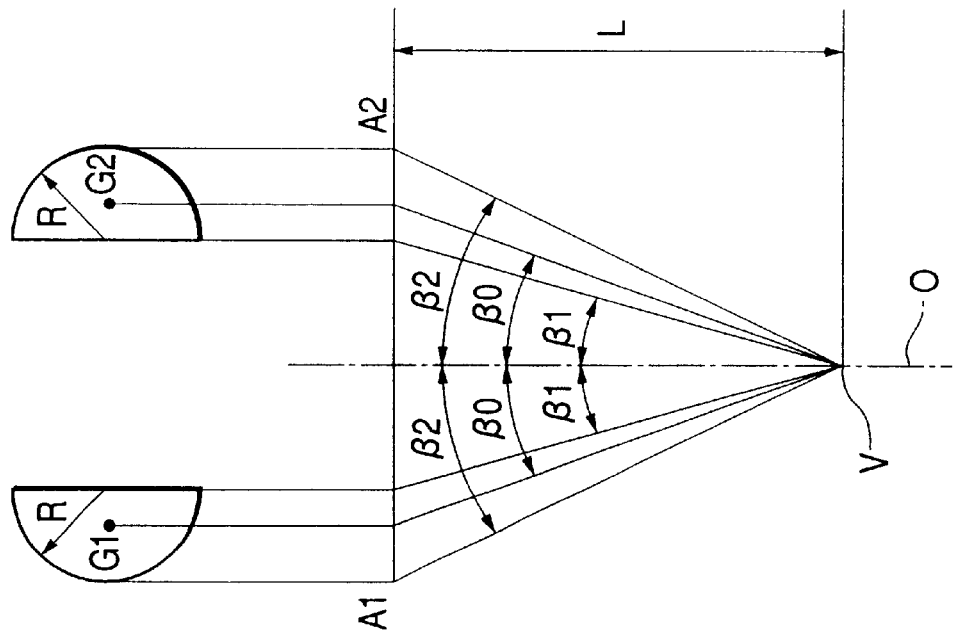
FIG. 16 is an explanatory view of the relationship among a portion to be measured, a measurement light source, a photomultiplier, and an entrance pupil.
Figure 17:
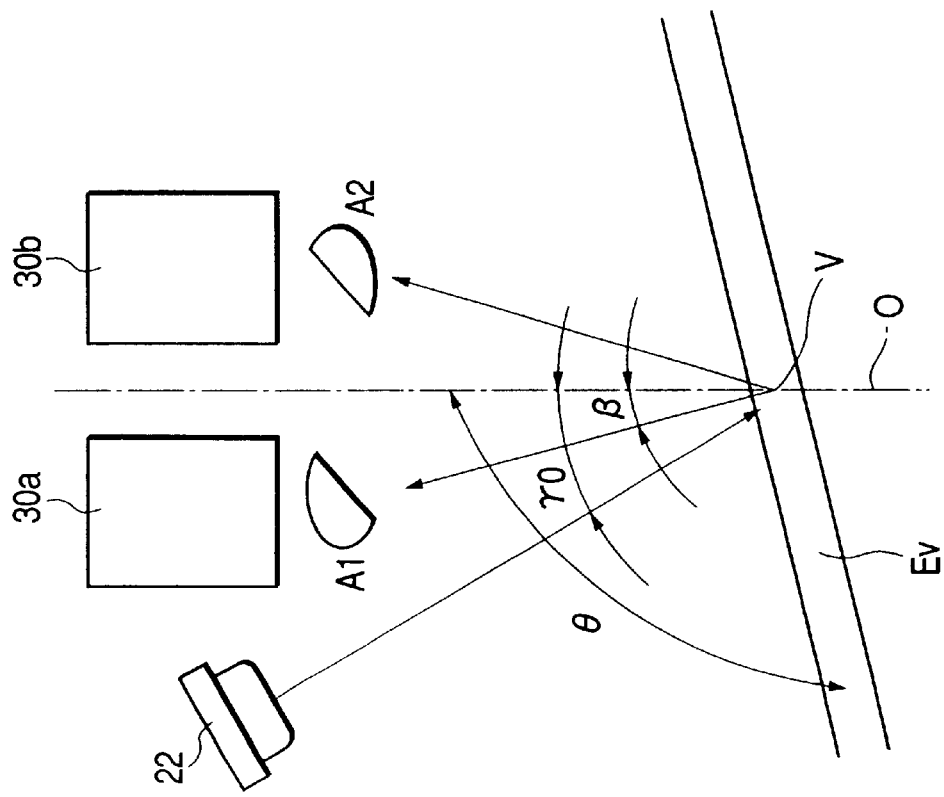
FIG. 17 is an explanatory view of the positional relationship of the entrance pupil.
Figure 18:
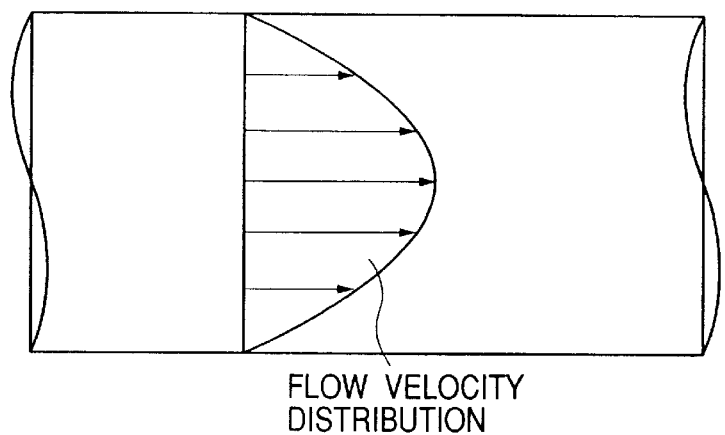
FIG. 18 is an explanatory view of the flow velocity distribution in a blood vessel.
Figure 19:
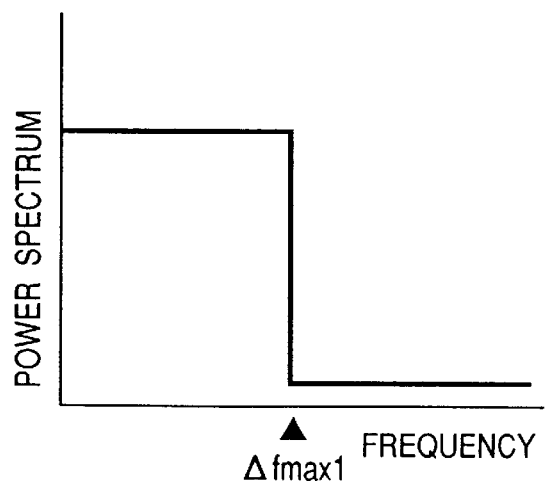
FIG. 19 is a graph showing the FFT waveform of a light beat signal.
Figure 20:
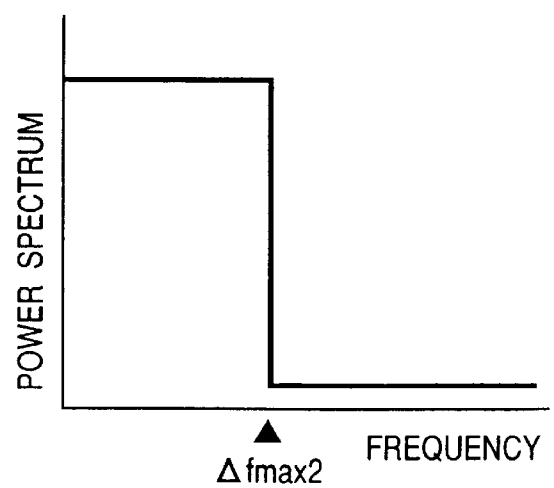
FIG. 20 is a graph showing the FFT waveform of a light beat signal.

FIG. 16 shows the relationship among the portion V to be measured of the blood vessel Ev to be measured, the measurement light source 22, the photomultipliers 30a and 30b, and entrance pupils A1 and A2 formed by the mirrors 29a and 29b. The entrance pupils A1 and A2 may be formed by stops, sensor portions of the photomultipliers, or the like in place of the reflecting mirrors. Let θ be the angle the optical axis O of the fundus blood flow meter makes with the direction in which the blood vessel Ev to be measured runs, i.e., the blood vessel angle as the reference of an angle, $γ_0$ be the angle the optical axis O makes with the direction of incidence of the measurement light source 22 to the portion V to be measured, i.e., the incident angle, and let β be the angle the optical axis O makes with the light-receiving direction from the portion V to be measured to the entrance pupils A1 and A2, i.e., the light-receiving angle. FIG. 17 is a plan view showing the positional relationship of the entrance pupils A1 and A2. The semicircular mirrors 29a and 29b are used to form semicircular entrance pupils A1 and A2 with a radius R. Information that pertains to the shape of these entrance pupils A1 and A2 is stored in the system controller 32. β0 represents the light-receiving angle of the center G1 or G2 of gravity of the entrance pupil A1 or A2. Note that the blood vessel angle θ in FIG. 16 is a parameter that differs depending on the direction in which the blood vessel Ev to be measured runs, and the light-receiving angle β is a parameter which differs depending on the light-receiving direction within the angle range from β1 to β2 with respect to the entrance pupils A1 and A2 in FIG. 17. Also, these angles θ, $γ_0$, and β use values converted into those in the human eye.

Assuming that scattered particles such as red blood cells or the like that flow in the blood vessel Ev travel at a velocity vector Ve, and assuming that Ki and Ks represent wave vectors in the directions the incoming light and scattered light travel, based on the principle of the Doppler effect, a Doppler shift Δf is given by:

$$Δf=(Ks-Ki)·Ve/(2π) \qquad (7).$$

In step S2, the theoretical ratio of the cutoff frequency is computed. Assume that a maximum angle θs of the practical angle range θs to θe (e.g., 75° to 105°) as the blood vessel angle θ is a temporarily defined blood vessel angle. If the blood vessel angle θ is given, from equation (7) using the angles θ, γ0, and β0, the theoretical ratio between the cutoff frequencies of FFTs based on light beat signals in the light-receiving directions of the centers G2 and G1 of gravity of the entrance pupils is given by:

$$\text{Ratio}=|\{\cos(\theta+\beta 0)+\cos(\theta-\gamma 0)\}/\{\cos(\theta-\beta 0)+\cos(\theta-\gamma 0)\}| \qquad (8)$$

and this value ratio is computed.

In step S3, using the first frequency Fs of the range from Fs to Fe of a predetermined frequency N1 as a temporarily defined cutoff frequency at the center G1 of gravity, a temporarily defined cutoff frequency N2 at the center G2 of gravity is computed by:

$$N2 = N1 \times \text{Ratio} \qquad (9)$$

In step S4, fitting curves as model shapes are respectively obtained for the FFT waveforms from the photomultipliers 30a and 30b, which have been processed in step S1. The method of obtaining a fitting curve is the same as that described in the above example.

From equation (7), of light beat signals respectively received by the photomultipliers 30a and 30b, cutoff frequencies Δf1 and Δf2 of FFTs based on the light beat signals in the light-receiving directions of the light-receiving angle β are respectively expressed using cutoff frequencies Δfo1 and Δfo2 at the light-receiving angles β0, and the angles θ, γ0, β, and β0 by:

$$\Delta f1 = \Delta of1 \cdot |\{\cos(\theta-\beta)+\cos(\theta-\gamma 0)\}/\{\cos(\theta-\beta 0)+\cos(\theta-\gamma 0)\}| \qquad (10)$$

$$\Delta f2 = \Delta of2 \cdot |\{\cos(\theta+\beta)+\cos(\theta-\gamma 0)\}/\{\cos(\theta+\beta 0)+\cos(\theta-\gamma 0)\}| \qquad (11)$$

The power spectrum P of an FFT of a light beat signal formed by a portion of the light-receiving angle β in the entrance pupil A1 or A2 is proportional to the area of that portion, and satisfies:

$$P \propto [R^2 - \{L(\tan\beta - \tan\beta 0)\}^2]^{1/2} \qquad (12)$$

where L is the distance between the plane formed by the entrance pupil A1 or A2, and the portion V to be measured.

The power spectrum P of the FFT of the light beat signal formed by the entire entrance pupils A1 and A2 is obtained by superposing power spectra within the range from the light-receiving angles β1 to β2 shown in FIG. 17, and the shape of a curve in which the power spectrum P of the FFT waveform continuously drops with a given slope near the cutoff frequency, i.e., theoretical cutoff shape, can be obtained.

In step S5, the square sums of the differences between the values of the power spectra P of the fitting curves of the FFT waveforms of the photomultipliers 30a and 30b, and the actual FFT waveform are computed, and a total To of the two square sums is obtained. By repeating steps S3 to S5 for the next frequency of the frequency Fs at a given interval until the last frequency Fe, fitting for the frequency is done. Also, by executing steps S2 to S5 for the range from θs to θe of the blood vessel angle θ, fitting for the blood vessel angle is done. Finally, values of square sums To having the blood vessel angle θ and frequency N1 as parameters are obtained.

After that, a minimum value of the square sums To is obtained in step S6, and the frequencies N1 and N2 at that time are determined to be cutoff frequencies Δfmax1 and Δfmax2 at the light-receiving angle β received by the photomultipliers 30a and 30b.

In step S7, a maximum blood flow velocity Vmax is computed by:

$$V_{max} = \{\lambda/(n \cdot 2\beta 0)\} \cdot |\Delta f_{max1} - \Delta f_{max2}| \qquad (13)$$

where γ is the wavelength of the measurement light beam, and n is the refractive index of the portion to be measured.

In this example, since fitting is done also using the blood vessel angle as a parameter, a method of obtaining a final blood flow velocity in consideration of this blood vessel angle is also available. The blood vessel angle θ corresponding to the minimum square sum To is defined as a blood vessel angle θv of the portion V to be measured, and two maximum blood flow velocities for Δfmax1 and Δfmax2 are computed by:

$$V_{max} = \lambda \cdot \Delta f_{max1}/\{n \cos(\theta v-\beta 0)+\cos(\theta v-\gamma 0)|\} \qquad (14)$$

$$V_{max} = \lambda \cdot \Delta f_{max2}/\{n|\cos(\theta v+\beta 0)+\cos(\theta v-\gamma 0)|\} \qquad (15)$$

Then, the average values of these velocities is used as a final maximum blood flow velocity.

What is claimed is:

1. A Doppler velocimeter comprising:
   an illumination system for illuminating a blood vessel with a light beam;
   a detector for detecting Doppler-shifted scattered light produced from blood flowing in the blood vessel; and
   a processor for obtaining a blood flow velocity by analyzing a signal from said detector, wherein said processor compares an actual power spectrum obtained by frequency-analyzing the signal with a theoretical power spectrum obtained using a frequency as a parameter while changing the parameter.

2. A velocimeter according to claim 1, wherein said detector detects said scattered light with a pupil having a predetermined shape and size, and the theoretical power spectrum has a curve of a slope that reflects the shape or size of the pupil.

3. A velocimeter according to claim 1, wherein said processor compares the actual power spectrum obtained by frequency-analyzing the signal with the theoretical power spectrum obtained using the frequency and the direction of the blood vessel with reference to an apparatus as parameters while changing the parameters.

4. A velocimeter according to claim 1, wherein the blood vessel is present on a fundus of an eye to be examined.

5. A velocimeter according to claim 1, wherein said processor repeats the comparison while changing the parameter, and computes a blood flow velocity using the frequency when it is determined as a result of comparison that the two power spectra best fit.

6. A velocimeter according to claim 5, wherein said processor compares a fitting curve generated in consideration of sufficiently high-frequency noise with a curve of the actual power spectrum.

7. A velocimeter according to claim 5, wherein the comparison is done by comparing a square sum of differences.

8. A velocimeter according to claim 5, wherein the frequency analysis includes FFT analysis.

9. A velocimeter according to claim 2, further comprising a stop which is inserted in front of said detector and forms the entrance pupil.

10. A velocimeter according to claim 1, wherein said detector consists of a single photomultiplier.

11. A velocimeter according to claim 1, wherein said detector has a plurality of photomultipliers.

12. A velocimeter according to claim 11, wherein said detector has two photomultipliers, and said processor computes to maintain a theoretical ratio between cutoff frequencies of the two photomultipliers upon comparison.

13. A Doppler velocimeter comprising:

an illumination system for illuminating a fluid with a light beam;

a detector for detecting Doppler-shifted scattered light produced from the fluid; and a processor for obtaining a flow velocity of the fluid by analyzing a signal from said detector, wherein said processor compares an actual power spectrum obtained by frequency-analyzing the signal with a theoretical power spectrum obtained using a frequency as a parameter while changing the parameter.

14. A fundus blood flow meter having the Doppler velocimeter according to any one of claims 1 to 13.

15. An eye examining apparatus having the Doppler velocimeter according to any one of claims 1 to 13.

* * * * *

UNITED STATES PATENT AND TRADEMARK OFFICE
CERTIFICATE OF CORRECTION

PATENT NO.   : 6,454,722 B1
DATED        : September 24, 2002
INVENTOR(S)  : Yasuyuki Numajiri et al.

It is certified that error appears in the above-identified patent and that said Letters Patent is hereby corrected as shown below:

Column 4,
Line 22, "7 After" should read -- 7. After --.

Column 13,
Line 32, "$\Delta of1.$" should read -- $\Delta fo1.$ --.
Line 33, "$\Delta of2.$" should read -- $\Delta fo2.$ --.

Column 14,
Line 18, "n cos" should read -- n | cos --.

Signed and Sealed this

Twenty-fifth Day of February, 2003

JAMES E. ROGAN
*Director of the United States Patent and Trademark Office*